(12) United States Patent
Parramon et al.

(10) Patent No.: US 8,369,963 B2
(45) Date of Patent: Feb. 5, 2013

(54) MULTI-ELECTRODE IMPLANTABLE STIMULATOR DEVICE WITH A SINGLE CURRENT PATH DECOUPLING CAPACITOR

(75) Inventors: Jordi Parramon, Valencia, CA (US); Kiran Nimmagadda, Valencia, CA (US); Emanuel Feldman, Simi Valley, CA (US); Yuping He, Northridge, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/012,279

(22) Filed: Jan. 24, 2011

(65) Prior Publication Data

US 2011/0118797 A1 May 19, 2011

Related U.S. Application Data

(63) Continuation of application No. 11/550,655, filed on Oct. 18, 2006, now Pat. No. 7,881,803.

(51) Int. Cl.
*A61N 1/40* (2006.01)
(52) U.S. Cl. ............... 607/61; 607/13; 607/46; 607/55; 607/56; 607/57
(58) Field of Classification Search ............ 607/13, 607/46, 55, 56, 57, 61
See application file for complete search history.

(56) References Cited

U.S. PATENT DOCUMENTS

| | | | |
|---|---|---|---|
| 3,983,881 A | 10/1976 | Wickham | |
| 4,114,627 A | 9/1978 | Lewyn et al. | |
| 5,193,539 A * | 3/1993 | Schulman et al. | 607/61 |
| 5,702,431 A | 12/1997 | Wang et al. | |
| 5,733,313 A | 3/1998 | Barreras, Sr. et al. | |
| 6,044,296 A | 3/2000 | Zhu et al. | |
| 6,185,452 B1 | 2/2001 | Schulman et al. | |
| 6,507,173 B1 | 1/2003 | Spiridon et al. | |
| 6,516,227 B1 | 2/2003 | Meadows et al. | |
| 6,553,263 B1 | 4/2003 | Meadows et al. | |
| 6,571,128 B2 | 5/2003 | Lebel et al. | |
| 6,622,048 B1 * | 9/2003 | Mann et al. | 607/46 |
| 7,024,246 B2 | 4/2006 | Acosta et al. | |
| 7,089,057 B2 | 8/2006 | Heathershaw et al. | |
| 7,120,992 B2 | 10/2006 | He et al. | |

(Continued)

FOREIGN PATENT DOCUMENTS

| | | |
|---|---|---|
| WO | 02/09808 | 2/2002 |
| WO | 2006/022993 | 3/2006 |

OTHER PUBLICATIONS

U.S. Appl. No. 09/624,130, filed Jul. 24, 2000, Kuzma.

*Primary Examiner* — Niketa Patel
*Assistant Examiner* — Hiba El-Kaissi
(74) *Attorney, Agent, or Firm* — Wong, Cabello, Lutsch, Rutherford, & Brucculeri, LLP

(57) ABSTRACT

Disclosed herein are circuits and methods for a multi-electrode implantable stimulator device incorporating one decoupling capacitor in the current path established via at least one cathode electrode and at least one anode electrode. In one embodiment, the decoupling capacitor may be hard-wired to a dedicated anode on the device. The cathodes are selectively activatable via stimulation switches. In another embodiment, any of the electrodes on the devices can be selectively activatable as an anode or cathode. In this embodiment, the decoupling capacitor is placed into the current path via selectable anode and cathode stimulation switches. Regardless of the implementation, the techniques allow for the benefits of capacitive decoupling without the need to associate decoupling capacitors with every electrode on the multi-electrode device, which saves space in the body of the device. Although of particular benefit when applied to microstimulators, the disclosed technique can be used with space-saving benefits in any stimulator device.

34 Claims, 16 Drawing Sheets

U.S. PATENT DOCUMENTS

| | | |
|---|---|---|
| 7,177,698 B2 | 2/2007 | Klosterman et al. |
| 7,379,775 B2 | 5/2008 | Parramon et al. |
| 7,437,193 B2 | 10/2008 | Parramon et al. |
| 7,532,936 B2 | 5/2009 | Erickson et al. |
| 2003/0204223 A1* | 10/2003 | Leinders et al. ............... 607/48 |
| 2004/0015205 A1 | 1/2004 | Whitehurst et al. |
| 2006/0276842 A1 | 12/2006 | He |
| 2007/0060980 A1 | 3/2007 | Strother et al. |
| 2007/0112404 A1 | 5/2007 | Mann et al. |

* cited by examiner

MULTI-ELECTRODE IMPLANTABLE STIMULATOR DEVICE WITH A SINGLE CURRENT PATH DECOUPLING CAPACITOR

CROSS REFERENCE TO RELATED APPLICATIONS

This application is a continuation of U.S. patent application Ser. No. 11/550,655, filed Oct. 18, 2006, to which priority is claimed, and which is incorporated herein by reference.

FIELD OF THE INVENTION

The present invention relates generally to implantable stimulator devices, e.g., an implantable pulse generator such as a Bion® device, a Spinal Cord Stimulation (SCS) device, or other type of neural stimulation devices.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder sublaxation, etc. The present invention may find applicability in all such applications, although the description that follows will generally focus on the use of the invention within a microstimulator device of the type disclosed in U.S. Published Patent Applications 2005/0021108, published Jan. 27, 2005; 2005/0057905, published Mar. 17, 2005; and 2004/0059392, published Mar. 25, 2004, which are all incorporated herein by reference in their entireties. However, the present invention also has applicability in other implantable stimulator devices, such as Spinal Cord Stimulation (SCS) devices, an example of which can be found in U.S. Pat. No. 6,553,263, which is incorporated herein by reference in its entirety.

Microstimulator devices typically comprise a small generally-cylindrical housing which carries electrodes for producing a desired electric stimulation current. Devices of this type are implanted proximate to the target tissue to allow the stimulation current to stimulate the target tissue to provide therapy for a wide variety of conditions and disorders. A "microstimulator" in the context of this application means an implantable stimulator device in which the body or housing of the device is compact (typically on the order of a few millimeters in diameter by several millimeters to a few centimeters in length) and usually includes or carries stimulating electrodes intended to contact the patient's tissue. However, a "microstimulator" may also or instead have electrodes coupled to the body of the device via a lead or leads, as shown in U.S. patent application Ser. No. 09/624,130, filed Jul. 24, 2000.

Some microstimulators in the prior art contain only one cathode electrode. More specifically, in such devices, and referring to FIG. 1, a single anode electrode 14 is provided for sourcing current into a resistance 16, R, i.e., the user's tissue. Typically, a return path for the current is provided by a single cathode 14', which could comprise another electrode on the device, but which might also comprised a portion of the conductive case for the device. Such a device is referred to herein as a "bi-electrode microstimulator," given its two electrodes 14 and 14'. As is known, the anode 14 sources or sinks current using a current generator circuit within a programmable Digital-to-Analog Converter, or "DAC" 20. The cathode 14' could also be connected to a current generator circuit or could simply be tied to a reference potential. An example of a bi-electrode microstimulator device includes the Bion® device made by Advanced Bionics Corporation of Sylmar, Calif.

Bi-electrode microstimulators benefit from simplicity. Because of their small size, the microstimulator can be implanted at a site requiring patient therapy, and without leads to carry the therapeutic current away from the body as mentioned previously. However, such bi-electrode microstimulators lack therapeutic flexibility: once implanted, the single cathode/anode combination will only recruit nerves in their immediate proximity, which generally cannot be changed unless the position of the device is manipulated in a patient's tissue.

To improve therapeutic flexibility, microstimulators having more than two electrodes have been proposed, and such devices are referred to herein as "multi-electrode microstimulators" to differentiate them from bi-electrode microstimulators discussed above. When increasing the number of electrodes in this fashion, the electrodes can be selectively activated once the device is implanted, providing the opportunity to manipulate therapy without having to manipulate the position of the device.

Drawings of an exemplary multi-electrode microstimulator 400 are shown in various views in FIGS. 2A-2C. As shown, the device 400 comprises a body or housing 402 which incorporates the power source (battery) and other circuitry needed for the device to function. On the exterior of the housing 402 are (in this example) eight conductive connectors 404 which are coupled to current generation circuitry in the housing (not shown). In this particular example, and as best shown in FIGS. 2B and 2C, a laminate 410 is positioned over the housing so as to bring the connectors 404 into contact with contact pads 412. The laminate 410 is akin to a printed circuit board and contains conductors 414 which ultimately meet with electrodes 416 designed to directly contact a patient's flesh. Thus, when the housing 402 and laminate 410 are coupled in this manner (FIG. 2C), the result is a multi-electrode microstimulator in which the various electrodes 416 are carried by and along the body of the device. Further details concerning this and other structures for a multi-electrode microstimulator are disclosed in the following references, which are incorporated herein in their entireties: U.S. Patent Publication No. 2004/0015205, published Jan. 22, 2004; U.S. patent application Ser. No. 11/142,154, filed Jun. 1, 2005; and U.S. patent application Ser. No. 11/280,620, filed Nov. 16, 2005. Additionally, a multi-electrode microstimulator need not employ electrodes on the body 402, and instead or in addition could comprise the structure of FIG. 2A with a lead or leads coupling to connectors 404 (not shown).

An issue concerning the design of any implantable stimulator, and especially microstimulators of the sort discussed above, involves the use of decoupling capacitors. One such decoupling capacitor 25, C, is shown in FIG. 1. As is known, decoupling capacitors are useful in implantable stimulator devices for a number of reasons. First, they can assist in charge recovery after the provision of a stimulation pulse, a point which is well known in the art and does not require further elaboration. Second, they provide additional safety by preventing the direct injection of current from the current generator circuit (e.g., inside of DAC 20) to the patient's tissue 16, R.

Examples of the use of decoupling capacitors in the implantable stimulator art are illustrated in FIGS. 3A and 3B. FIG. 3A shows an example of the use of decoupling capacitors 25 in a Spinal Cord Stimulation (SCS) device 30, such as the Precision® SCS device marketed by Advanced Bionics Corporation. As shown, this implantable stimulator comprises a plurality of electrodes 32, E1-En. Ultimately, a lead extension (not shown) can couple to the electrodes to carry the signals generated by an implantable pulse generator (IPG) to an electrode array (not shown) at the end of a lead. As a result, the electrode array can be tunneled into position (e.g., along the patient's spinal cord), while the IPG is implanted generally at a relative distance (e.g., in the patient's buttocks).

Associated with each electrode E1-En is a corresponding decoupling capacitor 25, C1-Cn. In an SCS device 30, the electrodes can be selectively activated, and any activated electrode can be selected as an anode or cathode. Indeed, more than one electrode can be selected as an anode at one time, and more that one electrode can be selected as a cathode at one time.

Thus, assume that electrode E2 is selected to act as an anode while electrode E4 is selected to act as a cathode as shown in FIG. 3A. Because each electrode E1-En is hard-wired with a decoupling capacitor C1-Cn, the resulting current path through the two electrodes E2 and E4 includes decoupling capacitors C2 and C4. This assists in charge recovery at both electrodes, and further provides redundant safety: even if one of the two capacitors C2 or C4 were to fail, the other would prevent the direct injection of current into the tissue R.

This approach of SCS device 30—in which a decoupling capacitor is associated with each electrode—is generally non-problematic. In an SCS device 30, because the IPG is not implanted at the site of required therapy and instead is positioned at a less critical portion of the patient (e.g., in the buttocks), the IPG can generally be made larger than can the body of the microstimulators discussed earlier. For instance, the IPG used in the SCS device 30 might be disk-shaped with a diameter of a few centimeters and a thickness of several millimeters. There is generally sufficient room in the IPG to accommodate the relatively large decoupling capacitors, C1-Cn. Thus, many currently marketed SCS devices 30 employ IPGs having 16 electrodes (17 counting the case electrode) and 16 corresponding decoupling capacitors (17 counting the case).

FIG. 3B illustrates another device 50 in which decoupling capacitors have been used in the implantable stimulator art, and specifically illustrates the use of a decoupling capacitor in the bi-electrode Bion® microstimulator device discussed earlier. As noted, bi-electrode microstimulator 50 comprises a single cathode 52 and anode 52'. As can be seen, a single decoupling capacitor C 25 is coupled to the cathode 52, and specifically is coupled between the cathode electrode 52 and the current generation circuitry 20. The anode, by contrast, is merely grounded or tied to a reference potential. Through the use of the decoupling capacitor, C, the same benefits noted earlier—improved safety and charge recovery—are had. (However, because only one decoupling capacitor is provided in the current path there is no redundant safety as provided by the two decoupling capacitors in the SCS device 30 of FIG. 3A).

As noted earlier, the body 55 of a bi-electrode microstimulator device 50 is very small, meaning there is a reduced volume within the body to accommodate multiple relatively-large decoupling capacitors 25. However, because such a device traditionally required the use of only a single decoupling capacitor, space within the body 55 was generally sufficient to accommodate this component.

However, the issue of limited space within the body of a microstimulator becomes very significant when a multi-electrode microstimulator is contemplated. Consider a multi-electrode microstimulator having eight cathodes and one anode (perhaps comprising the device's case). In such an architecture, and pursuant to the conventional wisdom of the prior art as understood by the Applicants, the microstimulator would need to have eight decoupling capacitors, one each hard-wired to each electrode. But as noted above, a microstimulator is intended to be quite small. This conflict either limits the number of electrodes a multi-electrode microstimulator can carry, or increases body size, neither of which is desirable.

Accordingly, the implantable stimulator art, and particularly the microstimulator art, would benefit from the ability to provide multiple electrodes while still providing sufficient capacitive decoupling that uses minimal volume inside the device. Embodiments of such a solution are provided herein.

SUMMARY

Disclosed herein are circuits and methods for a multi-electrode implantable stimulator device incorporating one decoupling capacitor in the current path established via at least one cathode electrode and at least one anode electrode. In one embodiment, the decoupling capacitor is hard-wired to a dedicated anode on the device. The cathodes are selectively activatable via stimulation switches. In another embodiment, any of the electrodes on the devices can be selectively activatable as an anode or cathode. In this embodiment, the decoupling capacitor is placed into the current path via selectable anode and cathode stimulation switches. Regardless of the implementation, the technique allows for the benefits of capacitive decoupling without the need to associate decoupling capacitors with every electrode on the multi-electrode device, which saves space in the body of the device. Although of particular benefit when applied to microstimulators, the disclosed technique can be used with space-saving benefits in any implantable stimulator device.

BRIEF DESCRIPTION OF THE DRAWINGS

The above and other aspects of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing the capacitive decoupling aspects that are central to this disclosure, the circuitry, structure, and function of an implantable stimulator device in which the inventive circuitry can be used is set forth for completeness.

As noted earlier, the disclosed implantable stimulator device may comprise a microstimulator device, an SCS device, or similar electrical stimulator and/or electrical sensor. However, for convenience, the inventive circuitry is disclosed herein in the context of a microstimulator. However, it is to be understood that the invention is not so limited. For example, the present invention may be used as part of a pacemaker, an implantable pump, a defibrillator, a cochlear stimulator, a retinal stimulator, a stimulator configured to produce coordinated limb movement, a cortical or deep brain stimulator, an occipital nerve stimulator, or in any other stimulator configured to treat urinary incontinence, sleep apnea, shoulder sublaxation, etc. Moreover, the technique can be used in non-medical and/or non-implantable devices as well.

Figure 4:
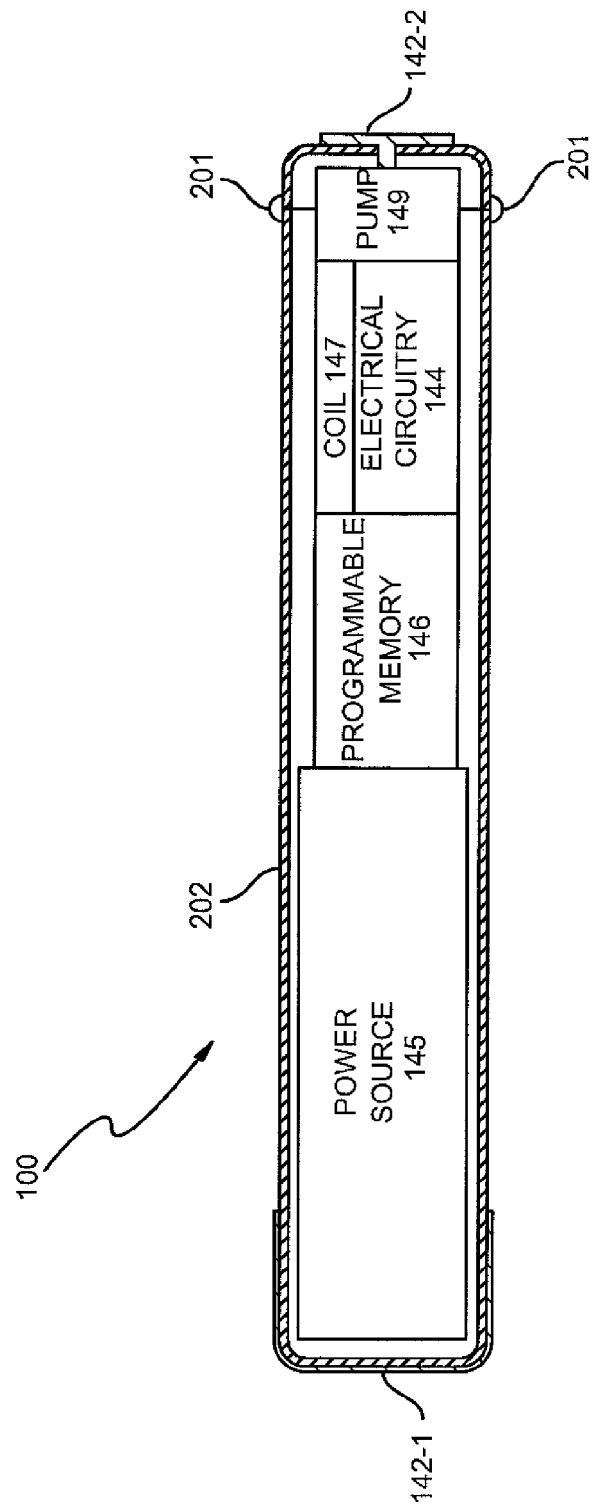
FIG. 4 illustrates an exemplary microstimulator in which the improved capacitive decoupling techniques of FIGS. 7-10 can be used.

FIG. 4 illustrates an exemplary implantable microstimulator 100. As shown, the microstimulator 100 may include a power source 145 such as a battery, a programmable memory 146, electrical circuitry 144, and a coil 147. These components are housed within a capsule 202, such as a thin, elongated cylinder or any other shape as best serves a particular application. The shape of the capsule 202 may be determined by the structure of the desired target tissue, the surrounding area, the method of implantation, the size and location of the power source 145 and/or the number and arrangement of external electrodes 142. In some embodiments, the volume of the capsule 202 is substantially equal to or less than three cubic centimeters.

Figure 1:
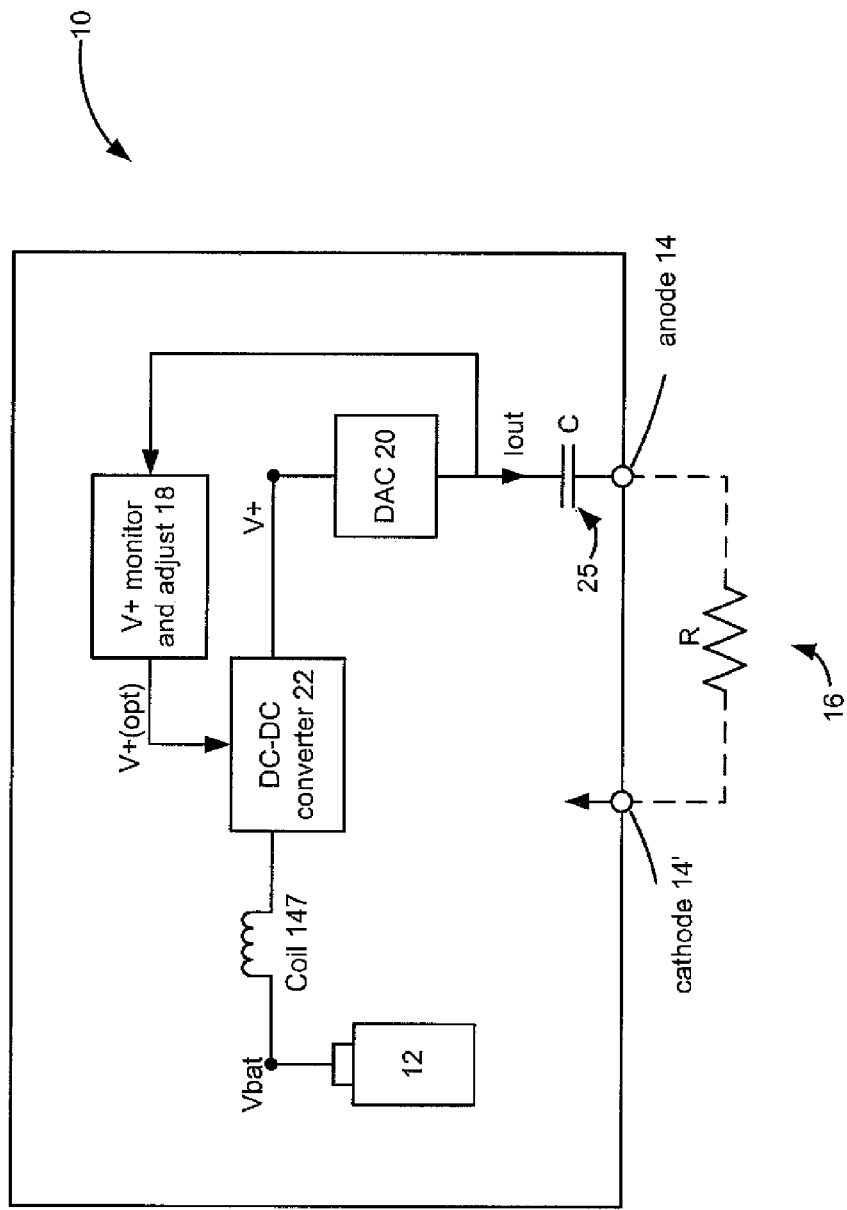
FIG. 1 illustrates the basic electrical components of a microstimulator in accordance with the prior art.
Figure 2A:
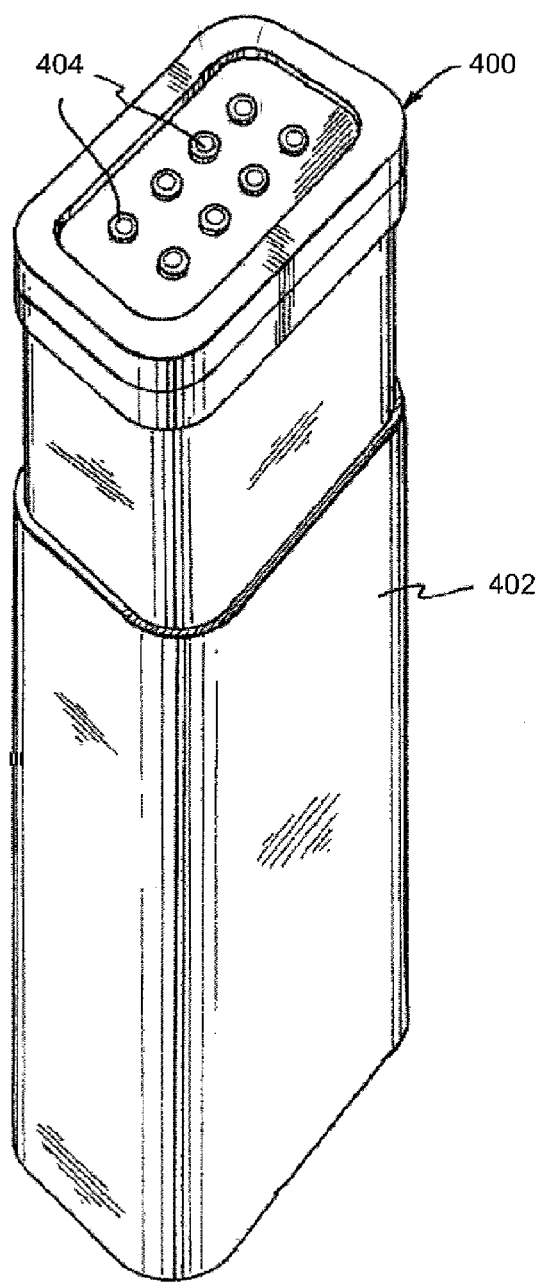
FIGS. 2A through 2C illustrate various views of a multi-electrode microstimulator in accordance with the prior art.
Figure 2B:
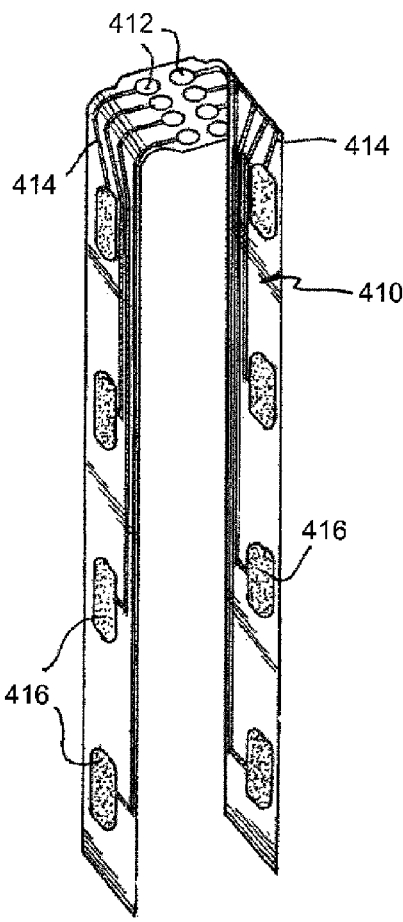
Figure 2C:
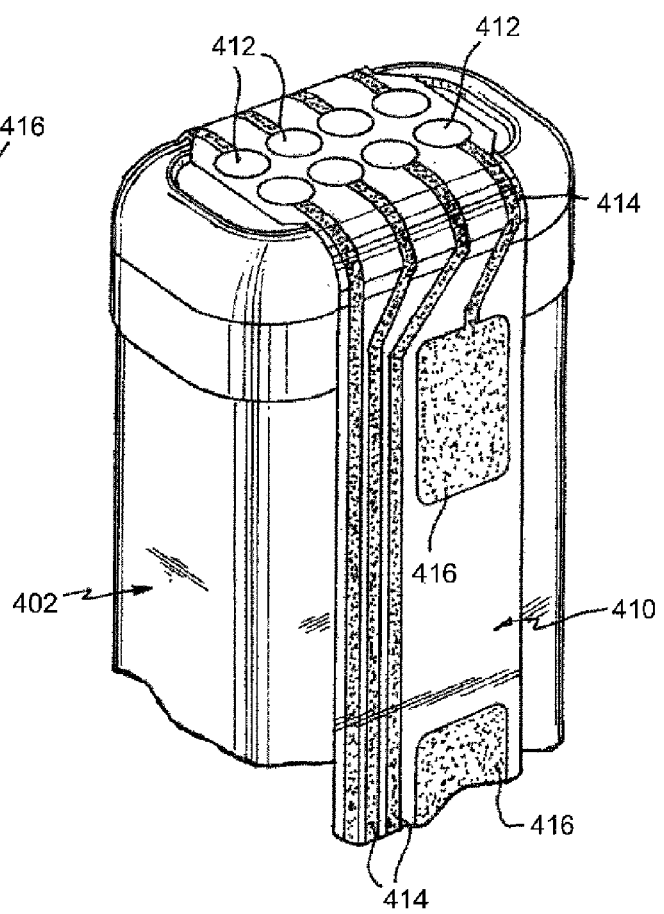

The power source 145, e.g., battery 12 of FIG. 1, is configured to output a voltage used to supply the various components within the microstimulator 100 with power. The power source 145 also provides power for any stimulation current applied with the microstimulator 100 to nearby tissue, as discussed in the Background section of this disclosure. The power source 145 may be a primary battery, a rechargeable battery, a capacitor, or any other suitable power source. Systems and methods for recharging the power source 145, where the source 145 is rechargeable, will be described below.

The coil 147 is configured to receive and/or emit a magnetic field (also referred to as a radio frequency (RF) field) that is used to communicate with or receive power from one or more external devices that support the implanted microstimulator 100, examples of which will be described below. Such communication and/or power transfer may include, but is not limited to, transcutaneously receiving data from the external device, transmitting data to the external device, and/or receiving power used to recharge the power source 145.

The programmable memory unit 146 is used for storing one or more sets of data, for example, electrical stimulation parameters as described further below. The programmable memory 146 allows a patient, clinician, or other user of the microstimulator 100 to adjust the stimulation parameters such that the electrical stimulation is at levels that are safe and efficacious for a particular medical condition and/or for a particular patient. Electrical stimulation parameters may be controlled independently. The programmable memory 146 may be any type of memory unit such as, but not limited to, random access memory (RAM), static RAM (SRAM), EEPROM, a hard drive, or the like.

The electrical stimulation parameters control various parameters of the stimulation current applied to a target tissue including, but not limited to, the frequency, pulse width, amplitude, burst pattern (e.g., burst on time and burst off time), duty cycle or burst repeat interval, ramp on time and ramp off time of the stimulation current, etc. To determine the strength and/or duration of electrical stimulation required to most effectively treat a particular medical condition, various indicators of the medical condition and/or a patient's response to treatment may be sensed or measured. These indicators include, but are not limited to, muscle or limb activity (e.g., electromyography (EMG)), electrical activity of the brain (e.g., EEG), neurotransmitter levels, hormone levels, and/or medication levels. In some embodiments, the microstimulator 100 may be configured to change the stimulation parameters in a closed loop manner in response to these measurements. Alternatively, other sensing devices may be configured to perform the measurements and transmit the measured values to the microstimulator 100.

Specific electrical stimulation may have different effects on different types of medical conditions. Thus, in some embodiments, the electrical stimulation may be adjusted by the patient, a clinician, or other user of the microstimulator 100 as best serves a particular medical condition. For example, the amplitude of the stimulus current applied to a target nerve may be adjusted to have a relatively low value to target relatively large-diameter fibers of the target nerve. The microstimulator 100 may also increase excitement of a target nerve by applying a stimulation current having a relatively low frequency to the target nerve (e.g., less than about 100 Hz). The microstimulator 100 may also decrease excitement of a target nerve by applying a relatively high frequency to the target nerve (e.g., greater than about 100 Hz). The microstimulator 100 may also be programmed to apply the stimulation current to a target nerve intermittently or continuously.

The microstimulator 100 includes electrodes 142-1 and 142-2 (akin to electrodes 14 and 14' of FIG. 1) on the exterior of the capsule 202. The electrodes 142 may be disposed at either end of the capsule 202, as illustrated in FIG. 4, or placed along the length of the capsule. There may also be more than two electrodes arranged in an array. One of the electrodes 142 may be designated as a stimulating electrode to be placed close to the target tissue or treatment site and one of the electrodes 142 may be designated as an indifferent electrode (reference node) used to complete a stimulation circuit. As shown earlier, multiple electrodes may be positioned along one or more sides of the microstimulator housing.

The electrical circuitry 144 is configured to produce electrical stimulation pulses that are delivered to the target nerve via the electrodes 142. In some embodiments, the microstimulator 100 may be configured to produce monopolar stimulation, which may be achieved, for example, using the stimulator case 202 as an indifferent electrode. The microstimulator 100 may alternatively or additionally be configured to produce bipolar stimulation, which may be achieved, for example, using one of the electrodes of the electrode array as a cathode and another as an anode.

The electrical circuitry 144 may include one or more microprocessors or microcontrollers configured to decode stimulation parameters and generate the corresponding stimulation pulses. In some embodiments, the microstimulator 100 has up to four or more channels and drives up to sixteen electrodes or more. The electrical circuitry 144 may include additional circuitry such as capacitors, integrated circuits, resistors, coils, and the like configured to perform a variety of functions as best serves a particular application.

In the example illustrated in FIG. 4, the microstimulator 100 includes two or more leadless electrodes 142. However, either or both of the electrodes 142 may alternatively be located at the ends of short, flexible leads. The use of such leads permits, among other things, electrical stimulation to be directed to targeted tissue(s) a short distance from the surgical fixation of the bulk of the device 100 at a more surgically convenient site. This minimizes the distance traversed and the surgical planes crossed by the device 100 and any lead(s).

The external surfaces of the microstimulator 100 are preferably composed of biocompatible materials. For example, the capsule 202 may be made of glass, ceramic, metal, or any other material that provides a hermetic package that excludes water vapor but permits passage of electromagnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The microstimulator 100 may also include one or more infusion outlets 201, which facilitate the infusion of one or more drugs into the target tissue. Alternatively, catheters may be coupled to the infusion outlets 201 to deliver the drug therapy to target tissue some distance from the body of the microstimulator 100. If the microstimulator 100 is configured to provide a drug stimulation using infusion outlets 201, the microstimulator 100 may also include a pump 149 that is configured to store and dispense the one or more drugs.

Of course, the microstimulator 100 of FIG. 4 is illustrative of many types of microstimulators that may be used to apply stimulation to target tissue to treat a particular medical condition. Other types of microstimulators, as well as details concerning microstimulator manufacture and operation can be found in the various patent documents incorporated by reference elsewhere in this disclosure.

Figure 5:
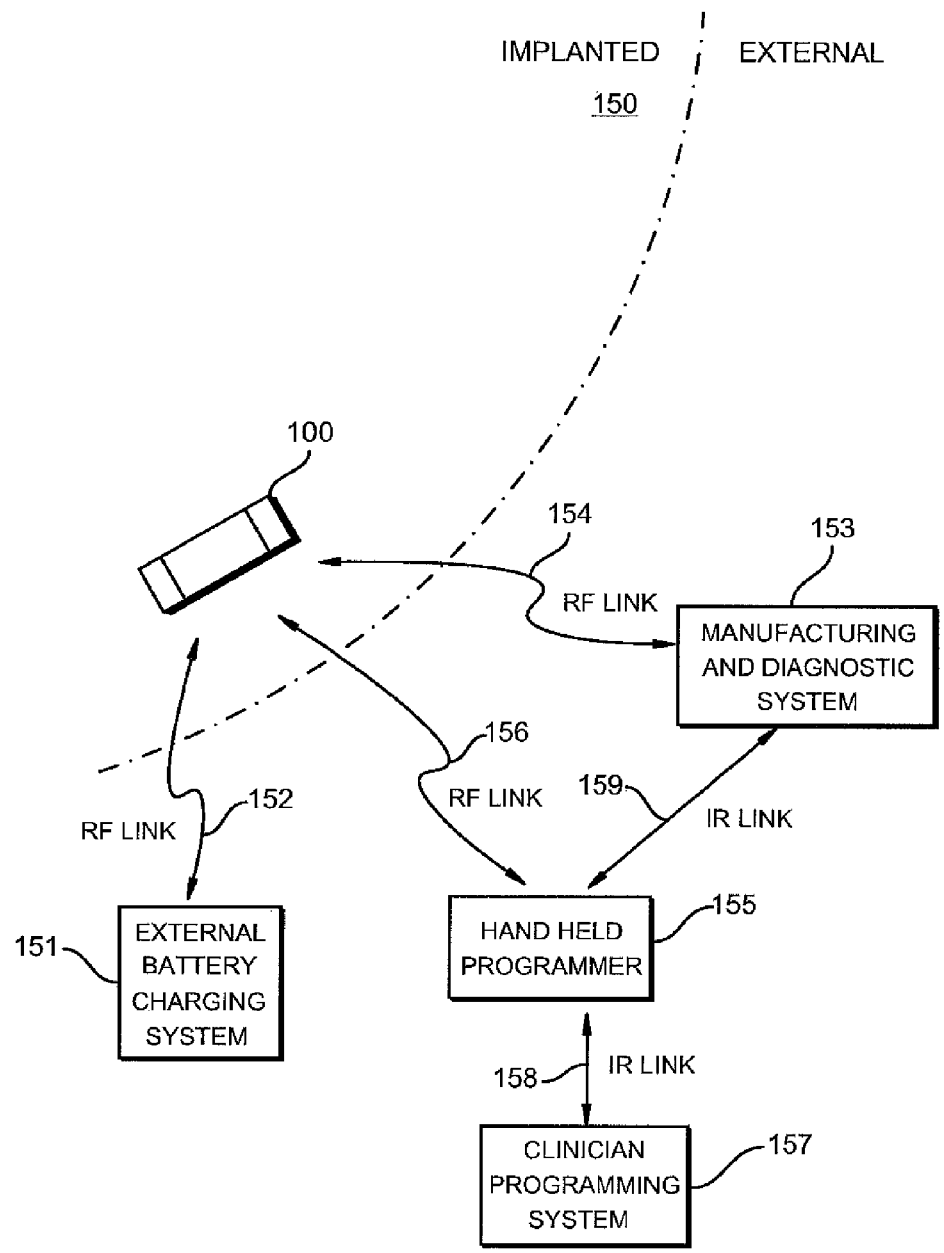
FIG. 5 illustrates the microstimulator of FIG. 4 and its interaction with various external components in a microstimulator communication system.

Turning to FIG. 5, the microstimulator 100 is illustrated as implanted in a patient 150, and further shown are various external components that may be used to support the implanted microstimulator 100. For example, an external battery charging system (EBCS) 151 may provide power used to recharge power source 145 (FIG. 4) via an RF link 152. As is known in the art, the RF link comprises electromagnetic energy which energizes the coil 147 (FIG. 4) through the patient 150's tissue, and which is rectified, filtered, and used to recharge the power source 145.

Other external components such as a hand held programmer (HHP) 155, clinician programming system (CPS) 157, and/or a manufacturing and diagnostic system (MDS) 153 may be used to activate, deactivate, program, and test the microstimulator 100 via one or more RF links 154, 156. Thus, one or more of these external devices 153, 155, 157 may also be used to control the microstimulator 100 to provide stimulation electrical pulses necessary to treat a particular medical condition, and may be used to provide or update the stimulation parameters and other data stored in the programmable memory (146, FIG. 4) of the microstimulator 100. Furthermore, the external devices 153, 155, 157 may communicate with each other. For example, the CPS 157 may communicate with the HHP 155 via an infrared (IR) link 158 or via any other suitable communication link. Likewise, the MDS 153 may communicate with the HHP 155 via an IR link 159 or via any other suitable communication link.

Additionally, the microstimulator 100 may report its status or various other parameters to any of the external devices via the two-way RF links 152, 154, and 156. For example, once the logic circuitry detects that the power source 145 is fully charged, the coil 147 (FIG. 4) is used to signal that fact back through the RF link to the EBCS 151 so that charging can cease. Likewise, once stimulation parameters are sent from either of the HHP 155 or the MDS 153, acceptance of those parameters can be reported back to those devices, and/or the actual parameters can be reported back as a double check.

The HHP 155, MDS 153, CPS 157, and EBCS 151 are merely illustrative of the many different external components that may be used in connection with the microstimulator 100. Furthermore, it will be recognized that the functions performed by the HHP 155, MDS 153, CPS 157, and EBCS 151 may be performed by combination devices or a single external device. One or more of these external devices may be embedded in a seat cushion, mattress cover, pillow, garment, belt, strap, pouch, or the like, so as to be conveniently placed near the implanted microstimulator 100 when in use.

With the implantable and external components of the system understood, an exemplary method in which the microstimulator 100 can be used to treat a particular medical condition is briefly illustrated. First, the microstimulator 100 is implanted so that its electrodes (142, FIG. 4) are coupled to or located near a target tissue. The microstimulator 100 is programmed with stimulation parameters to apply at least one stimulus to the target tissue. When the patient desires treatment with the programmed stimulation parameters, the patient sends a command to the microstimulator 100 (e.g., via a remote control) and the microstimulator 100 in turn delivers the prescribed stimulation. The microstimulator 100 may be alternatively or additionally configured to automatically apply the electrical stimulation in response to sensed indicators of the particular medical condition. To cease electrical stimulation, the patient may turn off the microstimulator 100 (again, via the remote control). When necessary, the EBCS 151 is activated to recharge the power source 145 as described above, and this can occur at convenient intervals for the patient 150, such as every night.

Figure 6:
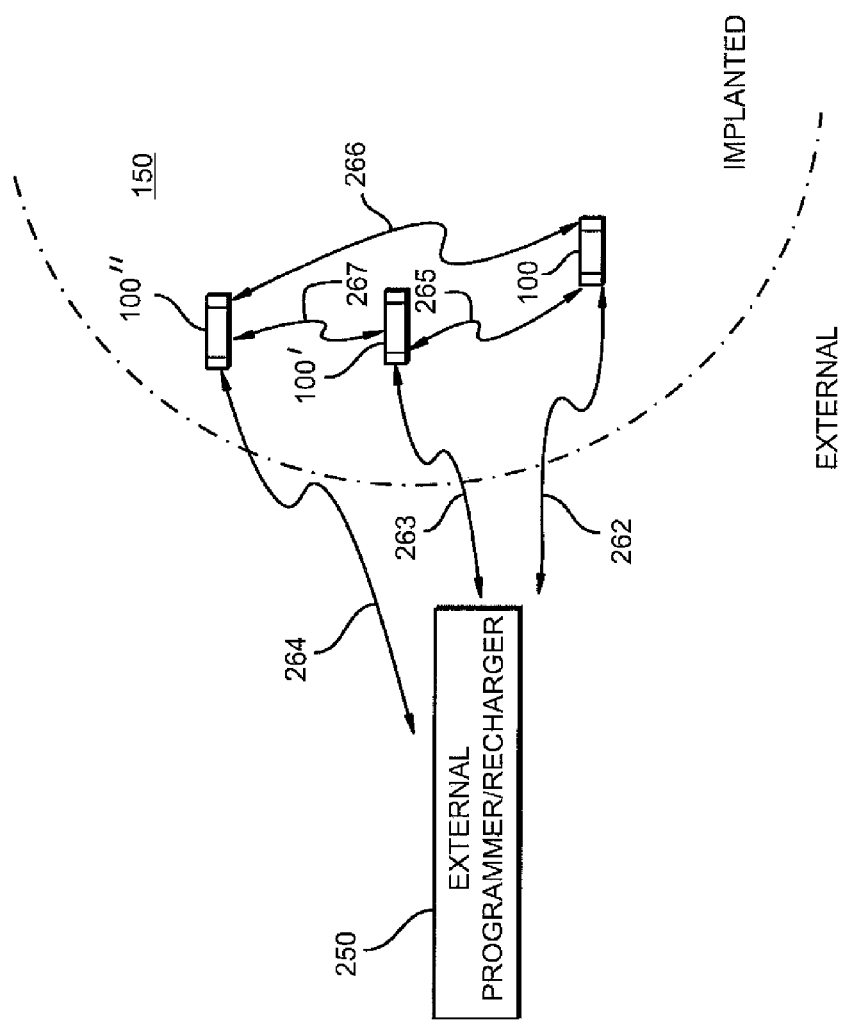
FIG. 6 illustrates several microstimulators of FIG. 4 used together in a communication network.

In some therapies, it may be desirable to employ more than one microstimulator 100, each of which could be separately controlled by means of a digital address. This allows multiple channels and/or multiple patterns of electrical stimulation to be used as is efficacious for certain medical conditions. For instance, as shown in the example of FIG. 6, a first microstimulator 100 implanted in a patient 150 provides a stimulus to a first location; a second microstimulator 100' provides a stimulus to a second location; and a third microstimulator 100" provides a stimulus to a third location. As mentioned earlier, the implanted devices may operate independently or may operate in a coordinated manner with other implanted devices or other devices external to the patient's body. That is, an external controller 250 (indicative of any of the external components of FIG. 5 or combinations of those components)

may be configured to control the operation of each of the implanted devices 100, 100', and 100" via RF links 262-264. In some embodiments, one implanted device, e.g. microstimulator 100, may control or operate under the control of another implanted device(s), e.g., microstimulator 100' and/or microstimulator 100", via RF links 265-267.

As a further example of multiple microstimulators 100 operating in a coordinated manner, the first and second microstimulators 100, 100' of FIG. 6 may be configured to sense various indicators of a particular medical condition and to transmit the measured information to the third microstimulator 100". The third microstimulator 100" may then use the measured information to adjust its stimulation parameters and to apply modified electrical stimulation to the target tissue accordingly.

Alternatively, the external device 250 may be configured to sense various indicators of a patient's condition. The sensed indicators can then be transmitted to one or more of the implanted microstimulators which may adjust stimulation parameters accordingly. In other examples, the external controller 250 may determine whether any change to stimulation parameters is needed based on the sensed indicators. The external device 250 may then signal a command to one or more of the microstimulators to adjust stimulation parameters accordingly.

With the basic structure and function of a microstimulator now in hand, focus now shifts to a detailed description of the capacitive decoupling techniques that are the focus of this disclosure.

As noted earlier, an issue in multi-electrode microstimulators involves the electrode decoupling capacitors. Such capacitors are relatively large and take up significant space within the body of the microstimulator. Thus, a problem is presented when a microstimulator has multiple electrodes, because conventional wisdom suggests a need for multiple decoupling capacitors.

Figure 7:
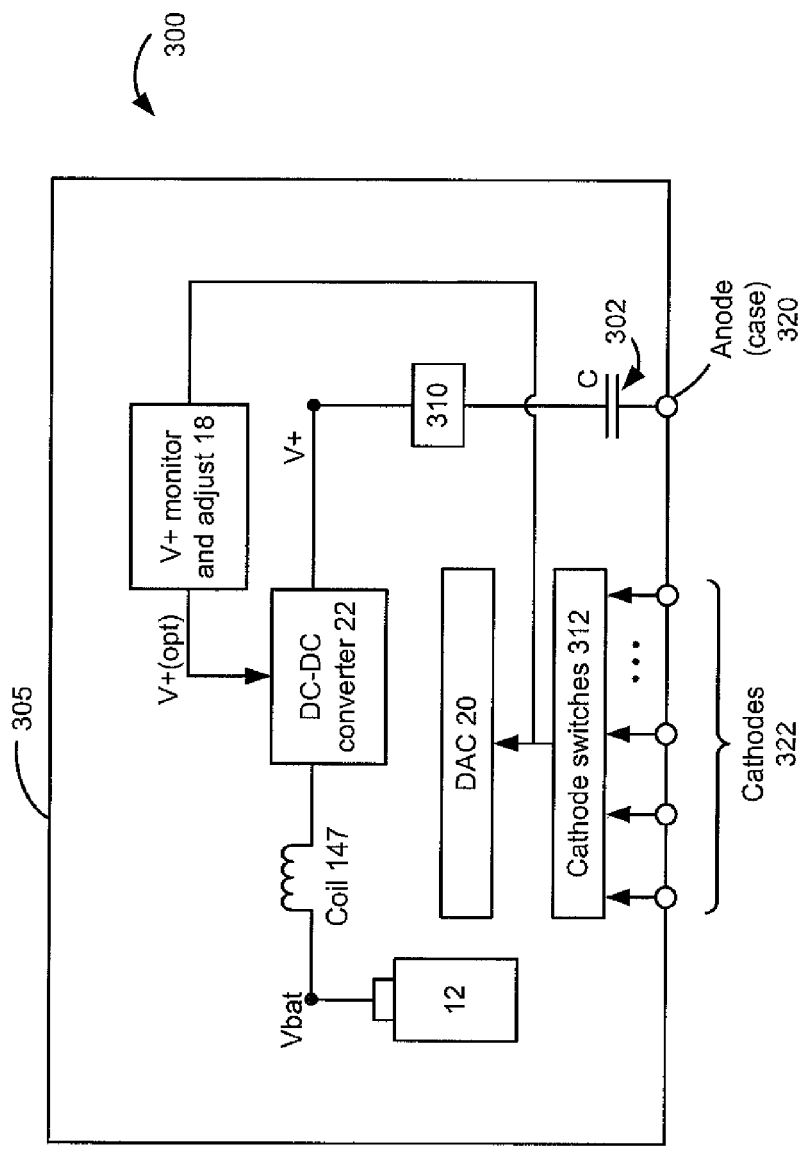
FIG. 7 illustrates an embodiment of the invention in which a single decoupling capacitor is used in a multi-electrode microstimulator.
Figure 8A:
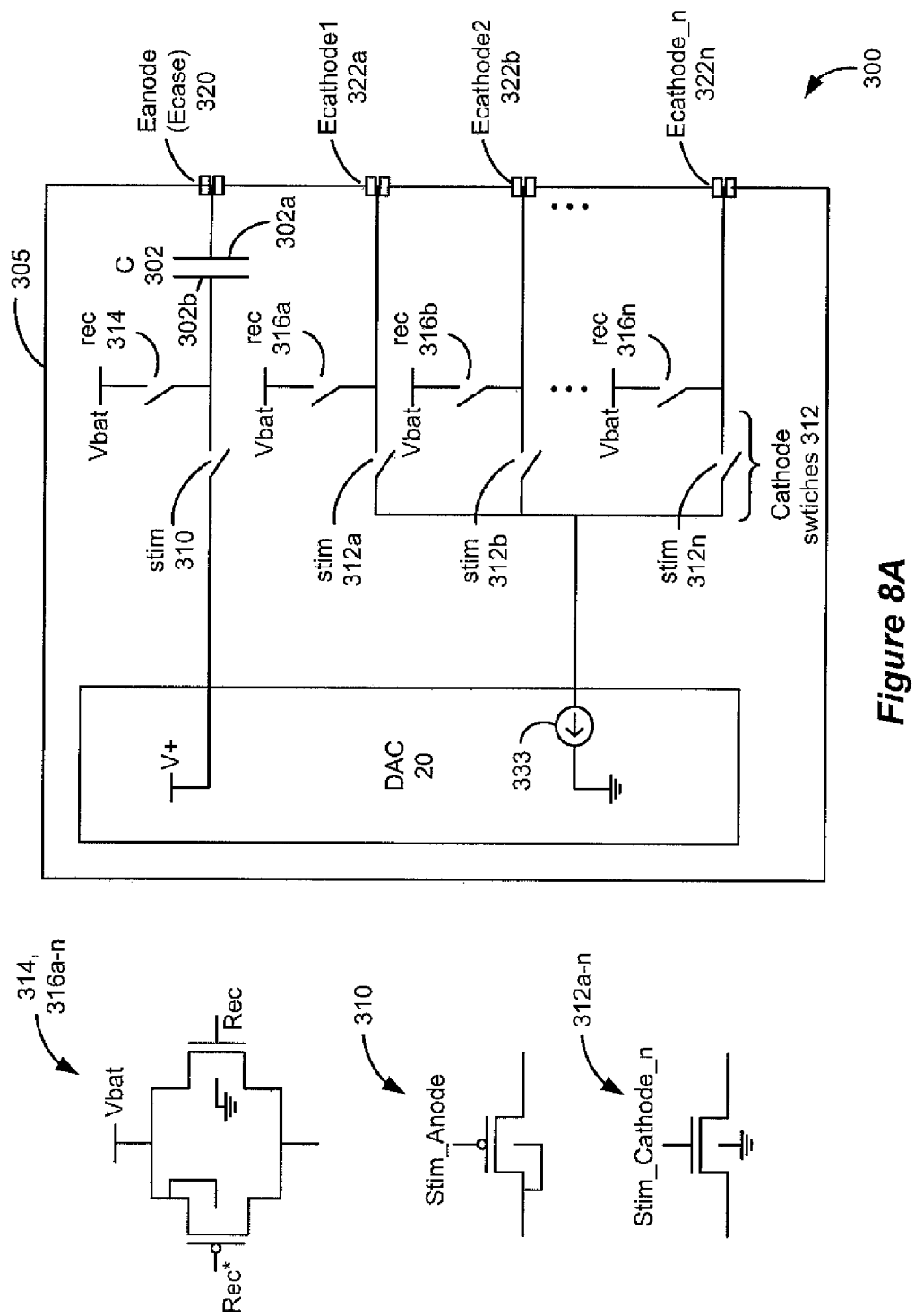
FIGS. 8A through 8C illustrate further circuitry details and modifications in a single anode/multi cathode multi-electrode microstimulator.

An embodiment of the invention contrary to such conventional wisdom is shown in FIG. 7, and in further circuitry detail in FIG. 8A. Shown is a multi-electrode microstimulator device 300 having a plurality of electrodes 320, 322a-n, which electrodes can be carried on its body 305 and/or on a lead(s). (For simplicity, in the embodiments as depicted in FIGS. 7-11, the electrodes are shown as carried on the body and without the use of leads). In this embodiment, the electrodes are split between a plurality ("n") of cathodes 322a-n (e.g., eight cathodes) and a dedicated anode 320, which like the cathodes can be carried on the body or lead-coupled to the body.

Despite the provision of a plurality of cathodes 322a-n, note that the embodiment provides a single decoupling capacitor 302. In this embodiment, a first plate 302a of the capacitor is hardwired to the dedicated anode 320, while the second plate 302b essentially communicates with the compliance voltage (V+) which in conjunction with the current generation circuitry 333 sets the current in the DAC 20. However, intervening between the second plate 302b and the compliance voltage V+ is a switch whose functions will be explained shortly.

Two types of switches are set forth in the embodiment of FIG. 8A: stimulation switches 310 and 312a-n, and recovery switches 314 and 316a-n. Both types of switches are apparent on the anode 320 and on the cathodes 322a-n. Thus, the anode path comprises a stimulation switch 310 and a recovery switch 314. Each of the cathode paths similarly comprises a stimulation switch 312a-n and a recovery switch 316a-n.

During provision of a stimulation pulse, the anode's stimulation switch 310 is closed, as is one of the cathode stimulation switches 312a-n. Which cathode stimulation switch is selected depends on which cathode has been deemed most appropriate for a given patient's therapy. For example, suppose experimentation reveals that a given patient feels the best relief when cathode 322b is activated. In this case, during active stimulation, switch 312b is closed, as well as switch 310 in the anode path. Other cathode stimulation switches 312a and 312c-312n remain open. The result is a current path through the anode stimulation switch 310, through anode 320, through the patient's tissue (not shown), through cathode 322b, through the cathode stimulation switch 312b associated with cathode 322b, and ultimately to ground as dictated by current generation circuitry 333 in the DAC 20. Notice that the decoupling capacitor 302 is present in the anode path (and hence in the overall current path). Thus, the benefits of capacitive decoupling discussed earlier (charge recovery; safety) are preserved in the disclosed embodiment.

Of course, it should be noticed that any of the cathodes 322 could be chosen via their associated stimulation switches 312. However, because the decoupling capacitor 302 is dedicated to the anode path, capacitive decoupling and its benefits are maintained, even though only one decoupling capacitor is used. This is a significant shift in conventional wisdom in the art, which suggests the use of 'n' different decoupling capacitors.

The recovery switches 314 and 316a-n are activated at some point after provision of a stimulation pulse, and have the goal of recovering any remaining charge left on the decoupling capacitor 302 and in the patient's tissue. Thus, after a stimulation pulse, the recovery switches 314 and 316a-n are closed. (Actually, only one of the cathode recovery switches 316a-n need be closed, preferably the switch corresponding to the previously-active cathode 322a-n. However, it is harmless and simple to close all of switches 316a-n during recovery). Closure of these switches places the same reference voltage on each plate of the decoupling capacitor 302, thus removing any stored charge. In one embodiment, for convenience, the reference voltage used is the battery voltage, Vbat, although any other reference potential could be used. Thus, Vbat is placed on the second plate 302b of decoupling capacitor 302 via anode recovery switch 314, and is likewise placed on the first plate 302a through the patient's tissue via cathode recovery switches 316a-n.

While the use of recovery switches 314, 316a-n has been described, such switches are not necessary to all useful embodiments of the invention, especially if charge recovery is not a significant concern in a particular application, or if other means are used to ensure charge recovery. In short, the recovery switches 314, 316a-n may be dispensed with in other useful embodiments of the invention. For example, and although not shown in FIG. 8A for simplicity, it can be beneficial to provide high-resistance "bleeder" resistors in parallel across the recovery switches 314 and 316a-n to allow charge to bleed off the capacitor 302 very slowly. This ensures that the capacitor 302 can eventually be discharged during all conditions, such as during periods of no stimulation. Of course, such bleeder resistors should be of high enough resistance to not significantly shunt the operation of the switches 314 and 316a-n during normal operation. In the embodiment of FIG. 8A, bleeder transistors, if used, could be present across the anode recovery switch 314 and at least one of the cathode recovery switches 316a-n.

The stimulation switches 310 and 312a-n and recovery switches 314 and 316a-n can comprise any switching structure or circuit such as transistors, transmission gates, etc. One embodiment showing circuitry that may be used for these switches is shown to the left of FIG. 8A. Thus, transistors are used for the stimulation switches 310, 312a-n, although a P-channel is used for the anode path switch 310, while N-channels are used for the cathode path switches 312a-n, which is sensible given the relative voltages present at those locations. The recovery switches 314 and 316a-n comprises transmission gates. The control (gate) signals for these various switches (Rec/Rec*, Stim_Anode, Stim_Cathode_n) are generated by a suitable microcontroller or any other from of digital controller present in the microstimulator 300 (not shown).

Figure 8B:
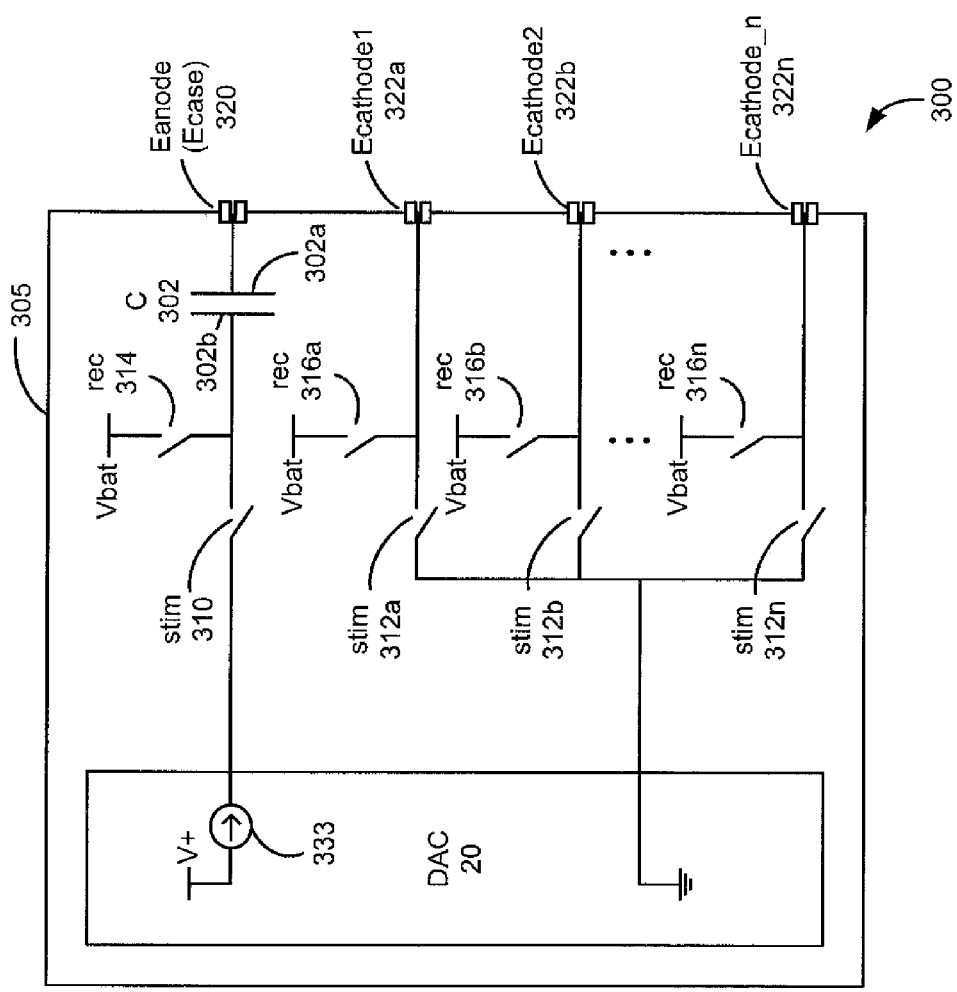
Figure 8C:
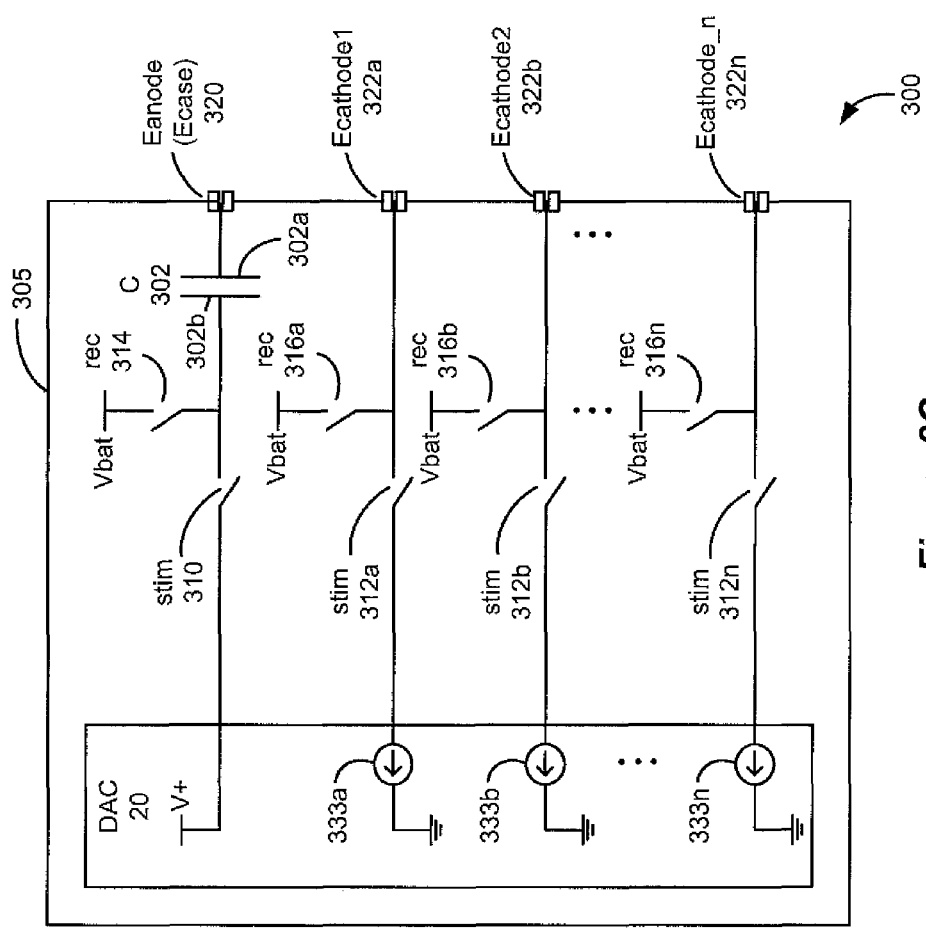

As shown in FIG. 8A, the current generation circuitry 333 is placed in the cathode path, i.e., in the opposite path from where the decoupling capacitor 302 is placed. However, as shown in FIG. 8B, the current generation circuitry 333 can also be placed in the anode path, i.e., in the same path where the decoupling capacitor 302 is placed. Indeed, FIGS. 8A and 8B can essentially be combined such that current generation circuitry 333 appears in both the cathode and anode paths. Moreover, the current generation circuitry 333 as shown in the cathode path can be distributed such that each cathode has its own dedicated and programmable current generation circuitry 333a-n, as shown in FIG. 8C.

Figure 9A:
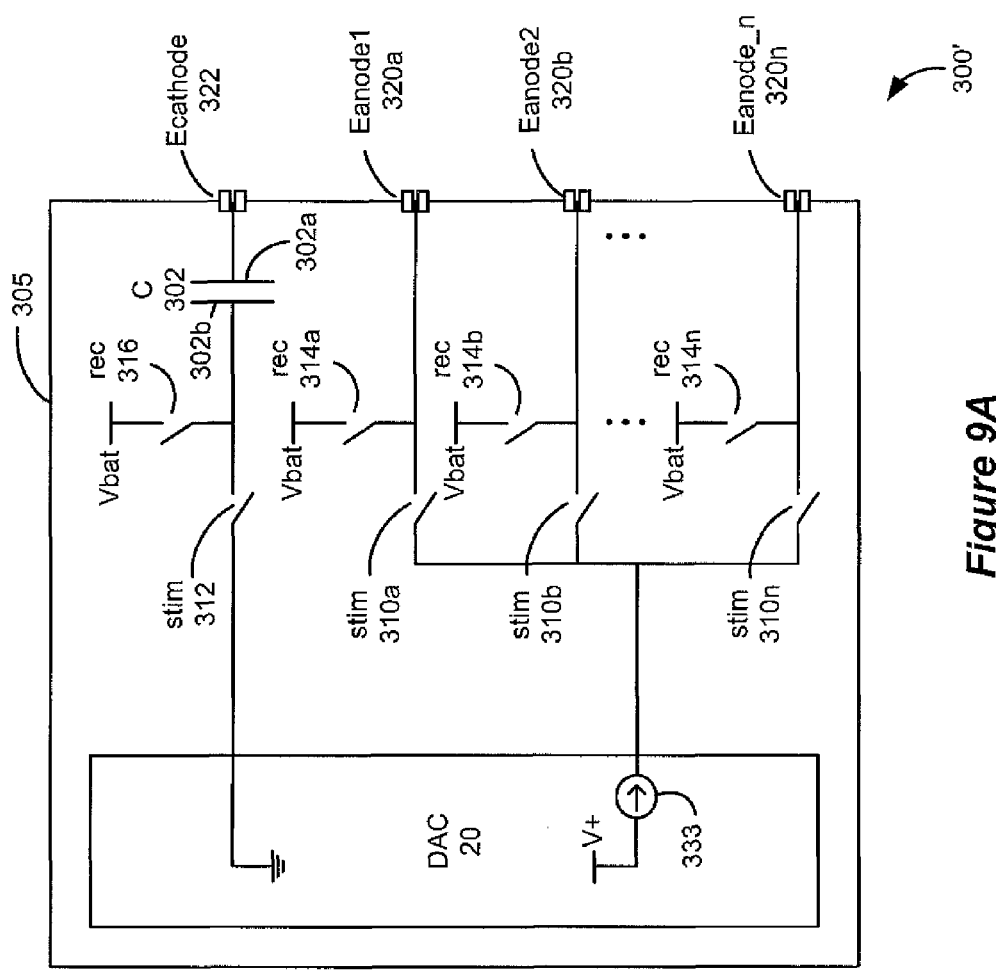
FIGS. 9A through 9C illustrate further circuitry details and modifications in a single cathode/multi anode multi-electrode microstimulator.
Figure 9B:
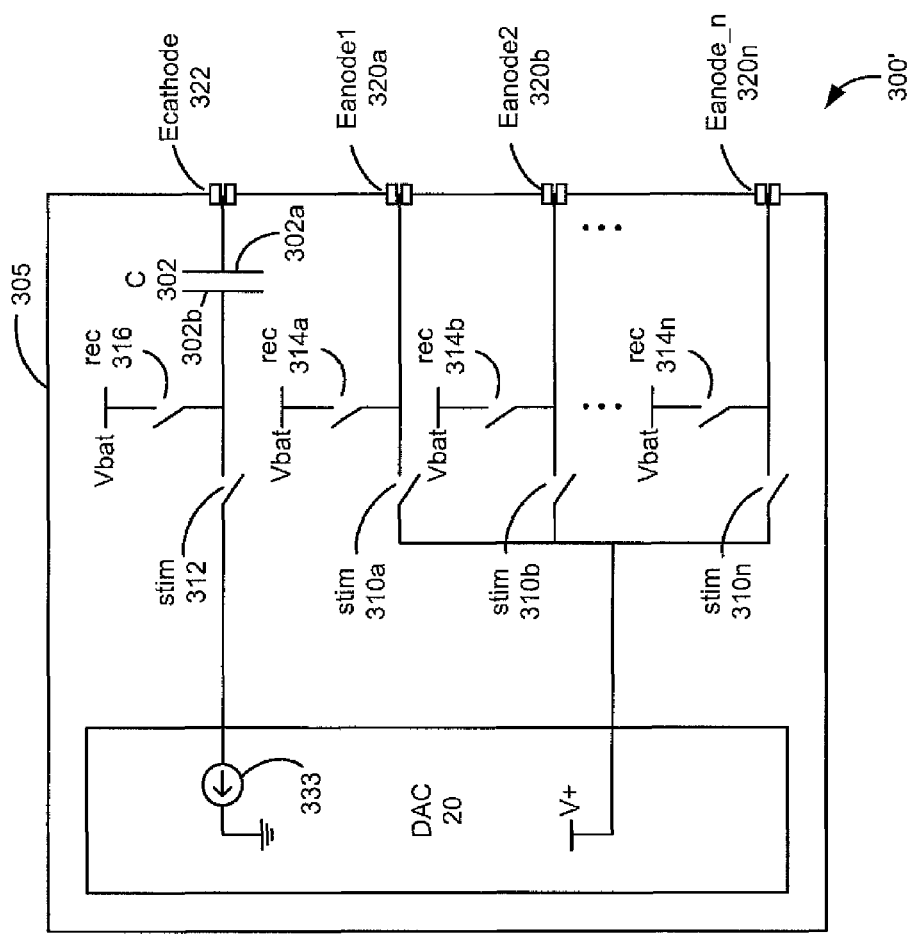
Figure 9C:
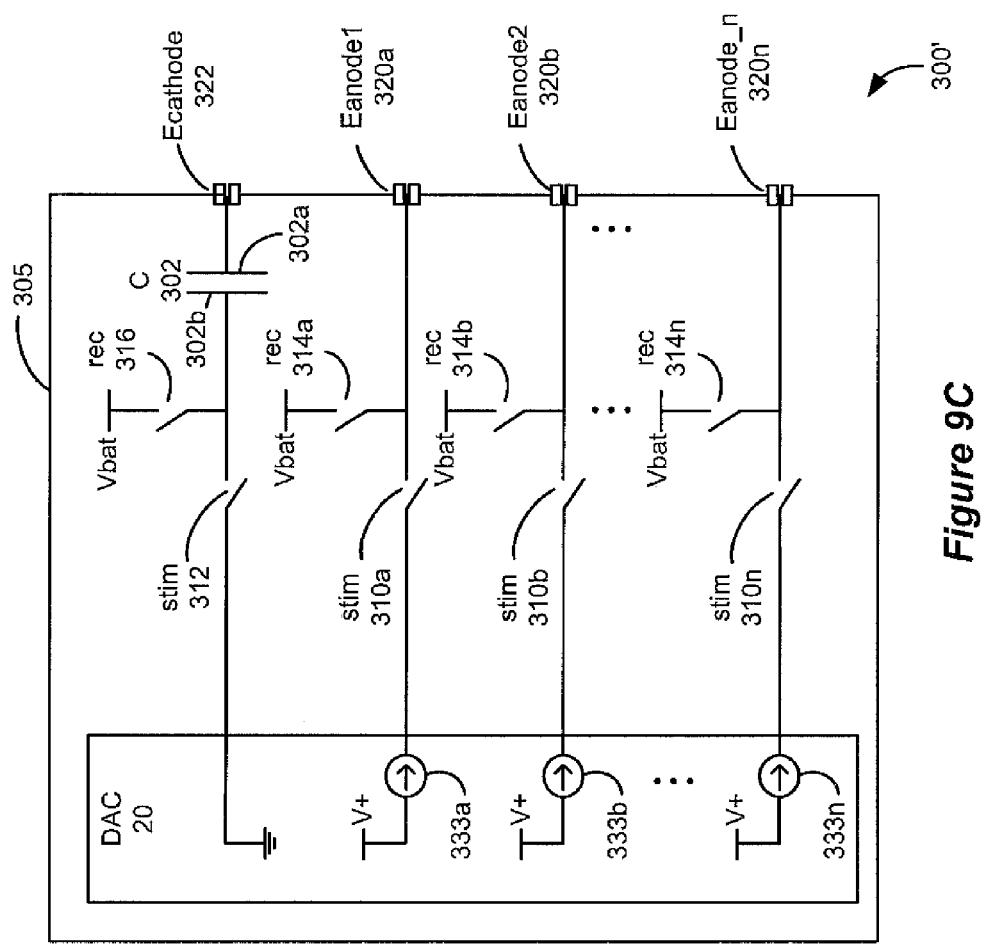

Moreover, and as shown in FIGS. 9A through 9C, the techniques disclosed can be employed to the case of a single cathode/multiple anode microstimulator 300'. Because these figures largely correspond to FIGS. 8A through 8C and should be clear to those of skill in the art, they are not further discussed.

As discussed above, in the embodiments of FIGS. 8A through 9C, an anode or cathode is specifically dedicated on the multi-electrode microstimulator. However, in other embodiments, it may be desirable to make a multi-electrode microstimulator more flexible. For example, if the multi-electrode microstimulator has eight electrodes, it may be desirable to designate any of the eight electrodes as the anode and any of the electrodes as the cathode. Such a design would provide the utmost flexibility for the multi-electrode microstimulator to recruit target nerves so as to best benefit the patient.

Figure 10:
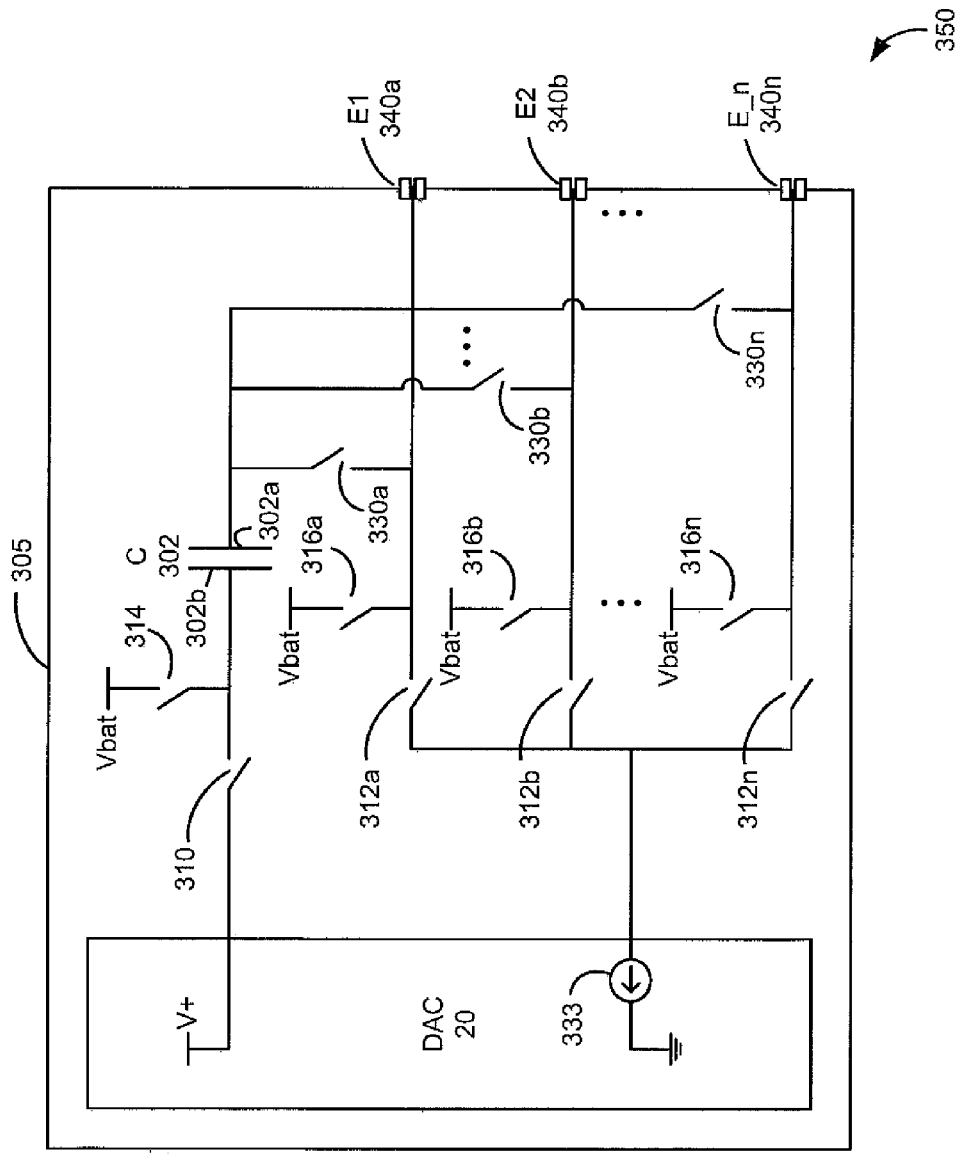
FIG. 10 illustrates a multi-electrode microstimulator using a single decoupling capacitor in an embodiment in which the anodes and/or cathodes are configurable.

FIG. 10 illustrates an embodiment of a multi-electrode microstimulator 350 providing such flexibility. Much of the circuitry in FIG. 10 is the same as that disclosed with respect to FIG. 8A, and so discussion of that circuitry is not repeated here. For example, optional recovery switches 314 and 316a-n and use of a single decoupling capacitor 302 are again utilized in device 350.

However, some differences are apparent. First, consistent with the configurable nature of the device 350, the electrodes 340a-n are not defined or pre-designated as anodes or cathodes; instead, any of the electrodes 340a-n can be programmed to function as either the anode or the cathode. Second, in addition to cathode stimulation switches 312a-n, anode selection switches 330a-n (e.g., implemented as P-channel transistors) are present between the first plate 302a of the decoupling capacitor 302 and the electrodes; by comparison, the first plate was hard wired in the embodiment of FIG. 8A. Using the cathode selection switches 312a-n and the anode selection switches 330a-n, the user may specify which of the 'n' electrodes will comprise the anode and the cathode. For example, the electrode E2 may be selected as the anode by closing anode selection switch 330b, while electrode E1 may be selected as the cathode by closing cathode selection switch 312a. At the same time, switches 330a and 312b would be kept open. In short, switches 312a-n and 330a-n comprise a switching matrix to allow any of the plurality of the electrodes to act as either the anode or the cathode.

Regardless of what electrode is selected as the anode or cathode, the decoupling capacitor 302 remains in the established current path. Accordingly, the benefits to capacitive decoupling discussed earlier are once again preserved in the embodiment of device 350. At the same time, only one decoupling capacitor 302 is needed to service the multiple electrodes, thus saving room within the body 305 of the microstimulator 350.

It should be noted that during current recovery, one or all of anode stimulation switches 330a-n would need to be closed as well as the recovery switches 314 and 316a-n to short the first 302a and second 302b plates of the decoupling capacitor.

The electrode configurable microstimulator 350 of FIG. 10 can of course also be modified in the various ways illustrated in FIGS. 8A-9C. For example, and as shown in FIGS. 8C and 9C, multiple current generation circuits could be utilized.

Figure 11:
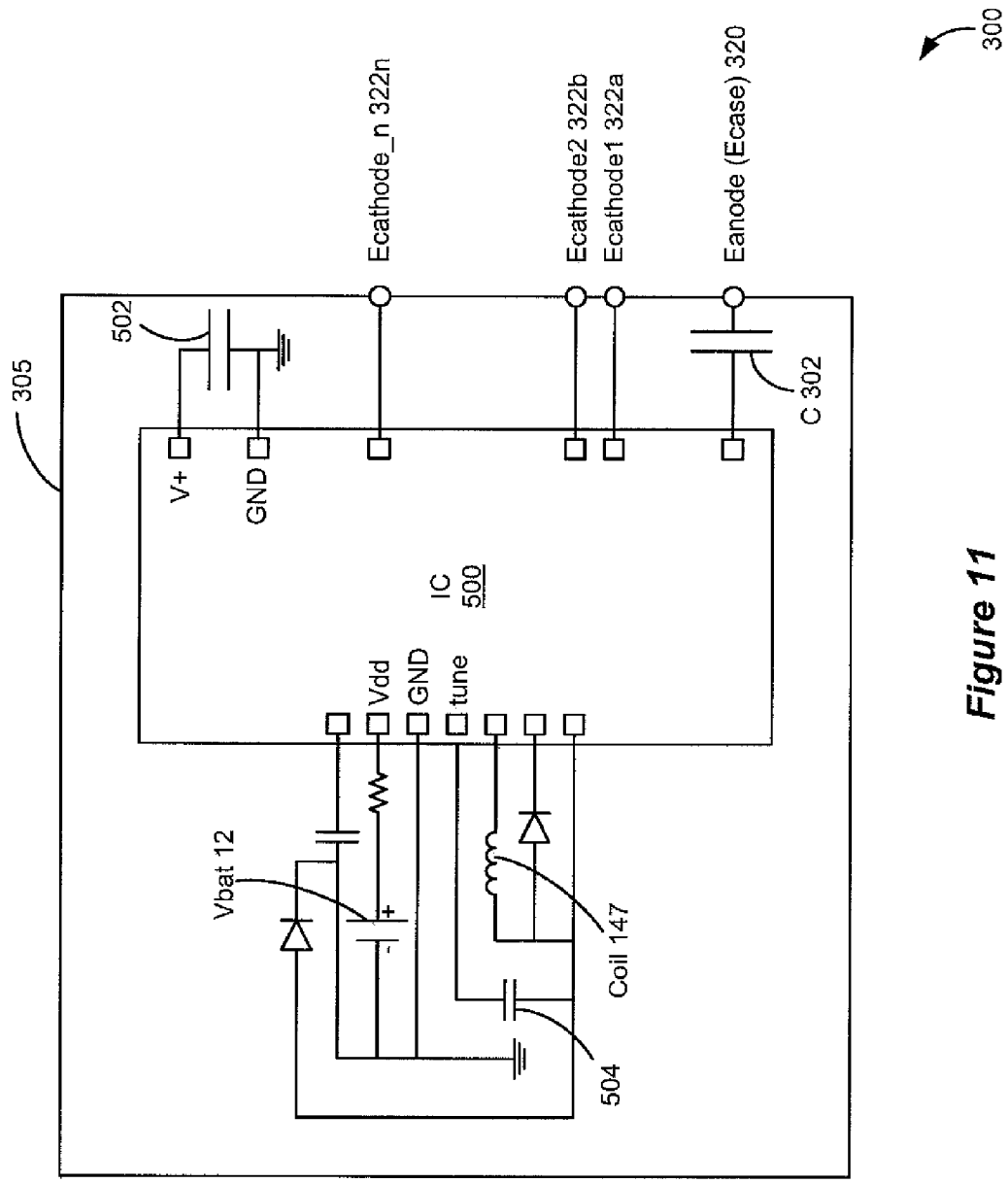
FIG. 11 illustrates a schematic of the multi-electrode microstimulator of FIG. 8A, and shows the provision of the decoupling capacitor in relation to a main integrated circuit.

A circuit schematic showing an implementation of the one-decoupling-capacitor technique disclosed herein is shown in FIG. 11. As shown, the multi-electrode microstimulator 300 may contain a main integrated circuit (IC) 500, which could include the device's logic functions, current generation and monitoring circuitry, etc. Coupled to the IC 500 are shown various exemplary discrete components relevant to rectification and tuning of RF communications (left side), and the electrodes (right side). One such discrete component comprises the singular decoupling capacitor C 302 that has been a focal point of this disclosure. However, it should be noted that other discrete components, and specifically other discrete capacitors, may also be present. For example, capacitors may be provided for compliance voltage stabilization (502) and for tuning the telemetry (RF link) coil 147 (504).

Figure 3B:
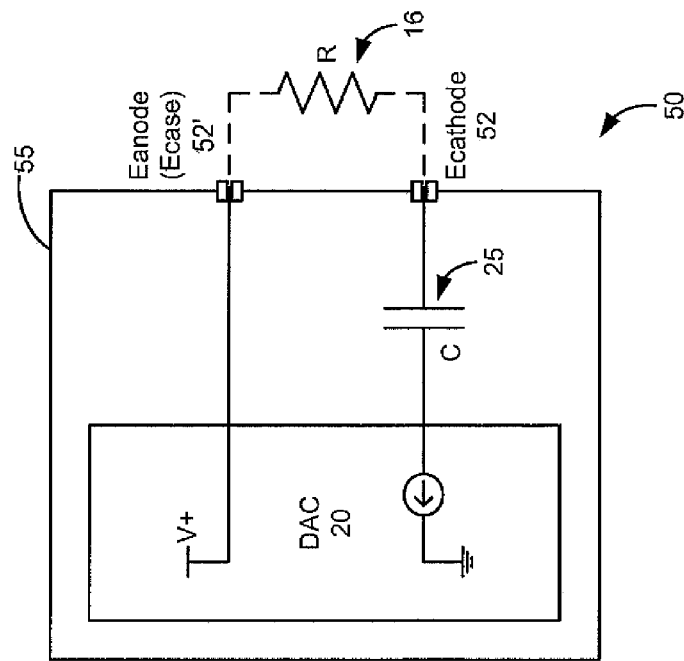
FIGS. 3A and 3B respectively illustrate the stimulation circuitry of a spinal cord stimulator (SCS) system and a bi-electrode microstimulator, and particularly show the decoupling capacitors as used in those techniques.
Figure 3A:
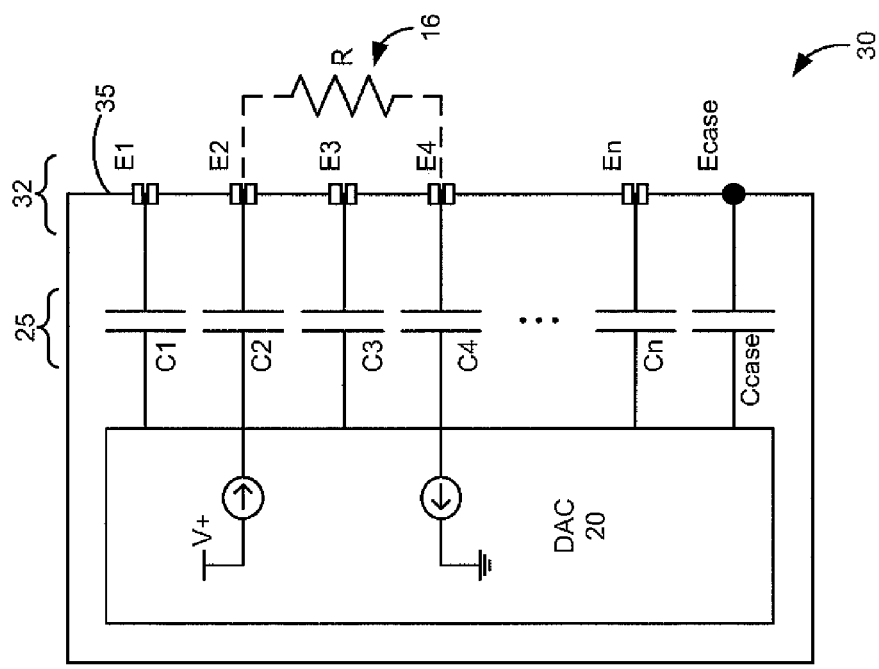

Embodiments of the invention using a single decoupling capacitor 302 in an implantable stimulator device have been discussed as particularly useful in the context of multi-electrode microstimulators. As noted, such devices have relatively small body volumes, and hence greatly benefit from the requirement to accommodate only one capacitor. However, the inventive aspects of this disclosure can also be used in implantable stimulator devices that do not comprise microstimulators. For example, in the SCS device 30 discussed earlier (FIG. 3A), it was noted that the body 35 of such a device may have room for decoupling capacitors dedicated to each electrode. However, that body 35 can be made even smaller using the disclosed techniques. For example, using embodiments of the invention, the number of decoupling capacitors C1-Cn could be reduced to one in an SCS device 30.

Alternatively, it should be noted that the disclosed techniques may not necessary result in the use of a single decoupling capacitor within a given device body, and instead the techniques may merely be implemented to reduce the number of decoupling capacitors within the device body. Consider the eight-electrode microstimulator of FIG. 8A. If desired, the circuitry as disclosed can be used for four electrodes, which circuitry can then be duplicated to form two sets of circuitry suitable for serving all eight electrodes. In this case, each set could include one decoupling capacitor 302, and thus there could be two capacitors, one for each set, with one capacitor to optimize the four electrodes in its set pursuant to the techniques disclosed herein. In this case, the device body would need to house only two decoupling capacitors. This is not as optimal as earlier embodiments employing a single decoupling capacitor from a space perspective, but it does mark an improvement compared to the conventional wisdom, which would employ the use of eight capacitors. Additionally, if the electrodes are grouped in sets in this manner, additional flexibility could be provided, such as the ability to simultaneously designate two cathodes (one in each set) and two anodes (again, one in each set).

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A stimulator device for providing a simulation current to the tissue of a patient, comprising:
 a body for the device;
 a plurality of electrodes coupled to the body, comprising:
  an anode, wherein the anode is coupled to an anode current path within the body, and
  a plurality of cathodes, wherein each cathode is coupleable to a single associated cathode current path within the body;
 selection circuitry for coupling one of the cathodes to its associated cathode current path, thereby selecting that cathode as an active cathode and that cathode current path as an active cathode current path; and
 a single decoupling capacitor within the body, wherein the anode current path comprises the decoupling capacitor, and wherein none of the cathode current paths comprise a decoupling capacitor,
 wherein the stimulation current flows from the anode current path to the active cathode current path.

2. The device of claim 1, wherein the plurality of electrodes are carried on the body.

3. The device of claim 1, further comprising a lead coupled to the body, wherein the plurality of electrodes are carried on the lead.

4. The device of claim 1, wherein the decoupling capacitor in the anode current path is directly coupled to the anode.

5. The device of claim 1, wherein the body is configured to be implantable in the patient.

6. The device of claim 1, wherein the anode is dedicated and not selectable.

7. The device of claim 1, further comprising recovery circuitry for shunting the anode and cathode current paths to a common potential after provision of the stimulation current.

8. The device of claim 1, further comprising current generation circuitry for generating the stimulation current.

9. The device of claim 8, wherein the current generation circuitry is located only in the anode current path.

10. The device of claim 8, wherein the current generation circuitry is located only in each cathode current path.

11. The device of claim 8, wherein the current generation circuitry is common to each cathode current path.

12. The device of claim 1, wherein the selection circuitry comprises a plurality of switches each coupled to one of the cathodes.

13. The device of claim 1, further comprising a switch in the anode current path, wherein the switch is closed during provision of the stimulation current.

14. A stimulator device for providing a simulation current to the tissue of a patient, comprising:
 a body for the device;
 a plurality of electrodes coupled to the body, comprising:
  a cathode, wherein the cathode is coupled to a cathode current path within the body, and
  a plurality of anodes, wherein each anode is coupleable to a single associated anode current path within the body;
 selection circuitry for coupling one of the anodes to its associated anode current path, thereby selecting that anode as an active anode and that anode current path as an active anode current path; and
 a single decoupling capacitor within the body, wherein the cathode current path comprises the decoupling capacitor, and wherein none of the anode current paths comprise a decoupling capacitor,
 wherein the stimulation current flows from the active anode current path to the cathode current path.

15. The device of claim 14, wherein the plurality of electrodes are carried on the body.

16. The device of claim 14, further comprising a lead coupled to the body, wherein the plurality of electrodes are carried on the lead.

17. The device of claim 14, wherein the decoupling capacitor in the cathode current path is directly coupled to the cathode.

18. The device of claim 14, wherein the body is configured to be implantable in the patient.

19. The device of claim 14, wherein the cathode is dedicated and not selectable.

20. The device of claim 14, further comprising recovery circuitry for shunting the cathode and anode current paths to a common potential after provision of the stimulation current.

21. The device of claim 14, further comprising current generation circuitry for generating the stimulation current.

22. The device of claim 21, wherein the current generation circuitry is located only in the cathode current path.

23. The device of claim 21, wherein the current generation circuitry is located only in each anode current path.

24. The device of claim 21, wherein the current generation circuitry is common to each anode current path.

25. The device of claim 14, wherein the selection circuitry comprises a plurality of switches each coupled to one of the anodes.

26. The device of claim 14, further comprising a switch in the cathode current path, wherein the switch is closed during provision of the stimulation current.

27. A stimulator device for providing a simulation current to the tissue of a patient, comprising:
 a body for the device;
 a plurality of electrodes coupled to the body, wherein each electrode is coupleable to a single associated anode current path within the body and a single associated cathode current path within the body;
 selection circuitry for coupling a first of the electrodes to its associated anode current path and for coupling a second of the electrodes to its associated cathode current path, thereby selecting the first electrode as an active anode and its associated anode current path as an active anode current path, and thereby selecting the second electrode as an active cathode and its associated cathode current path as an active anode current path; and
 a single decoupling capacitor within the body, wherein either the active anode current path or the active cathode current path comprises the decoupling capacitor, and wherein neither the other of the active anode current path or the active cathode current path, nor any other of the anode or cathode current paths, comprise a decoupling capacitor,
 wherein the stimulation current flows from the active anode current path to the active cathode current path.

28. The device of claim 27, wherein the plurality of electrodes are carried on the body.

29. The device of claim 27, further comprising a lead, wherein the plurality of electrodes are carried on the lead.

30. The device of claim 27, wherein the decoupling capacitor is directly coupled to the anode if in the active anode current path, and is directly coupled to the cathode if in the active cathode current path.

31. The device of claim 27, wherein the body is configured to be implantable in the patient.

32. The device of claim 27, further comprising recovery circuitry for shunting the anode and cathode current paths to a common potential after provision of the stimulation current.

33. The device of claim 27, further comprising current generation circuitry for generating the stimulation current.

34. The device of claim 27, wherein the selection circuitry comprises an anode selection switch and a cathode selection switch associated with each electrode.

* * * * *